(12) United States Patent
Kakuto et al.

(10) Patent No.: US 8,388,522 B2
(45) Date of Patent: Mar. 5, 2013

(54) ENDOSCOPE SYSTEM, PROGRAM AND ENDOSCOPE SYSTEM CONTROL METHOD

(75) Inventors: Atsushi Kakuto, Hachioji (JP); Mitsuhiro Ito, Akiruno (JP); Seiichi Ito, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 1222 days.

(21) Appl. No.: 12/168,471

(22) Filed: Jul. 7, 2008

(65) Prior Publication Data

US 2008/0262307 A1 Oct. 23, 2008

Related U.S. Application Data

(63) Continuation of application No. PCT/JP2006/324679, filed on Dec. 11, 2006.

(30) Foreign Application Priority Data

Jan. 13, 2006 (JP) ................................. 2006-006789

(51) Int. Cl.
*A61B 1/12* (2006.01)

(52) U.S. Cl. ......................... 600/159; 600/156; 600/158

(58) Field of Classification Search .................. 600/118, 600/156–159, 115–116; 604/99.01–99.04
See application file for complete search history.

(56) References Cited

U.S. PATENT DOCUMENTS

2001/0039370 A1* 11/2001 Takahashi et al. ............ 600/159
2006/0100485 A1* 5/2006 Arai et al. ..................... 600/159

FOREIGN PATENT DOCUMENTS

| EP | 1 077 041 A1 | 2/2001 |
|----|----|----|
| JP | 04-361732 | 12/1992 |
| JP | 6-75572 | 9/1994 |
| JP | 11-276427 | 10/1999 |
| JP | 2000189380 A * | 7/2000 |

OTHER PUBLICATIONS

English-language abstract only of Japanese Patent Application Publication No. 04-054950 dated Feb. 21, 1992.

* cited by examiner

*Primary Examiner* — Matthew J Kasztejna
*Assistant Examiner* — Ryan Henderson
(74) *Attorney, Agent, or Firm* — Scully, Scott, Murphy & Presser, P.C.

(57) ABSTRACT

An endoscope system having a two-stage depression button provided in an operation portion of an endoscope; a first switch changing from off to on by a first stage depressing operation of the depression button and maintaining the on state after the first stage; a second switch changing from off to on by a second stage depressing operation of the depression button; and a control unit controlling to provide an air feeding function when the first switch is on and provide a water feeding function without providing the air feeding function regardless of a state of the first switch when the second switch is on, the control unit controlling to provide the air feeding function with a delay of a predetermined time period so long as the first switch does not change from on to off within the predetermined time period when the first switch changes from off to on.

5 Claims, 6 Drawing Sheets

FIG.6
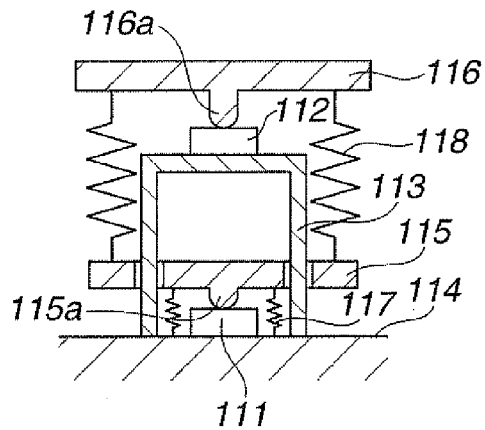
FIG.7
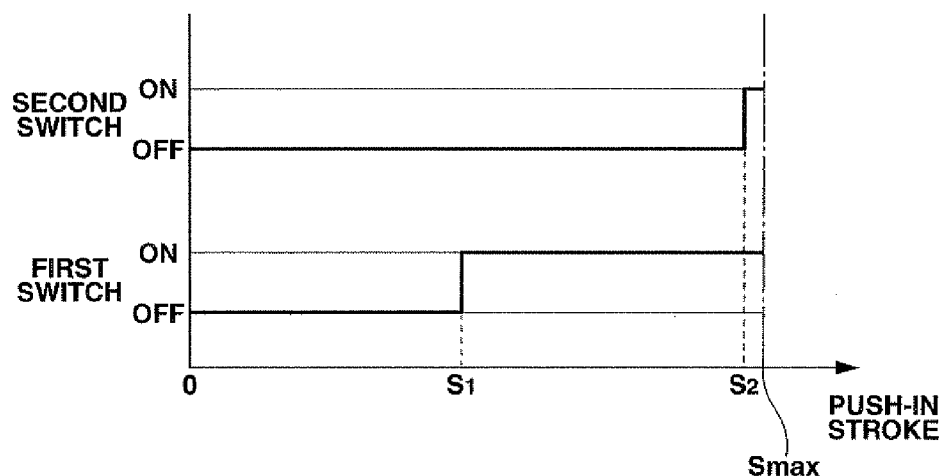
FIG.8
| AIR FEEDING/ WATER FEEDING BUTTON | WATER FEEDING | |
|---|---|---|
| | AIR FEEDING | |
| | NO OPERATION | |
| LEAK VALVE | OPEN | |
| | CLOSE | |
| AIR FEEDING CONTROL VALVE | OPEN | 0.3s |
| | CLOSE | |
| WATER FEEDING CONTROL VALVE | OPEN | |
| | CLOSE | |

ENDOSCOPE SYSTEM, PROGRAM AND ENDOSCOPE SYSTEM CONTROL METHOD

CROSS REFERENCE TO RELATED APPLICATION

This application is a continuation application of PCT/JP2006/324679 filed on Dec. 11, 2006 and claims benefit of Japanese Application No. 2006-006789 filed in Japan on Jan. 13, 2006, the entire contents of which are incorporated herein by this reference.

BACKGROUND OF THE INVENTION

1. Field of the Invention

The present invention relates to an endoscope system having a multistage operating member for providing the functions of an endoscope, a program and an endoscope system control method.

2. Description of the Related Art

An endoscope has been widely used in the field of medicine, for example, to observe regions which cannot be directly viewed such as those in a lumen. Such an endoscope is generally configured having an elongated insertion portion to be inserted into a subject and an operation portion for performing operation on a hand side. Such an operation portion is often provided with an air feeding/water feeding button for performing air feeding/water feeding, a suction button for performing suction and the like. The air feeding/water feeding button is configured as a two-stage depression button and configured such that air feeding by a first stage depression and water feeding by a second stage depression are performed by means of a mechanical mechanism. In addition, such a conventional medical-purpose endoscope is subjected to sterilization and the like for reuse each time the same is used.

In contrast to this, an endoscope is proposed in which an insertion portion to be inserted into a subject is detachably attached to an operation portion.

An example of such an endoscope is a rotary self-propelled endoscope wherein a rotating cylindrical body having a spiral-form portion and rotatable about an axis is provided on an outer peripheral side of an insertion portion and rotation of the rotating cylindrical body enables automatic insertion through an anus into a large intestine. In the rotary self-propelled endoscope, the insertion portion having the rotating cylindrical body is detachably attached to an operation portion and configured to be disposable.

Also in a detachable-insertion-portion-type endoscope, it is conceivable to provide an air feeding conduit line, a water feeding conduit line and a suction conduit line similarly to a typical endoscope. In this case, if conduit lines for connecting with these conduit lines are provided in the operation portion, the operation portion has to be sterilized each time the endoscope is used, thereby reducing an effect of making the insertion portion disposable.

Therefore, in such a detachable-insertion-portion-type endoscope, it is considered preferable to enable conduit lines from the insertion portion to be connected to an air feeding/water feeding device or a suction device not via an interior of the operation portion.

However, in an endoscope having an operation portion in which no conduit line exists, an operating button of a conduit line system in the operation portion needs to be changed from control by means of a mechanical mechanism which is general in conventional endoscopes to some other means so that control of the conduit line system can be properly performed. Particularly, with respect to the above described two-stage depression button such as the air feeding/water feeding button, a special contrivance is considered to be necessary in order to provide the functions of the endoscope satisfactorily.

The present invention is made in view of the above circumstances, and has for its object to provide an endoscope system which can provide the functions of an endoscope satisfactorily using a multistage operating member which is not mechanically controlled.

SUMMARY OF THE INVENTION

In order to achieve the above object, an endoscope system according to the present invention includes: a two-stage depression button provided in an operation portion of an endoscope; a first switch disposed at a first stage depressing operation position in the depression button and configured so as to change from off to on by the first stage depressing operation and maintain an on state after the first stage; a second switch disposed at a second stage depressing operation position in the depression button and configured so as to change from off to on by the second stage depressing operation; and control means which performs control so as to provide a first function of the endoscope when the first switch is on and provide a second function of the endoscope without providing the first function regardless of a state of the first switch when the second switch is on, the control means performing control so as to provide the first function with a delay of a predetermined time period so long as the first switch does not change from on to off within the predetermined time period when the first switch changes from off to on, the predetermined time period being longer than a time period expected to be required for the depression button to move in a stroke from the first stage to the second stage.

In addition, a program according to the present invention is a program for causing a computer to control an endoscope system including a two-stage depression button provided in an operation portion of an endoscope, a first switch disposed at a first stage depressing operation position in the depression button and configured so as to change from off to on by the first stage depressing operation and maintain an on state after the first stage, a second switch disposed at a second stage depressing operation position in the depression button and configured so as to change from off to on by the second stage depressing operation, the program being for causing the computer to carry out: a step of providing a first function of the endoscope with a delay of a predetermined time period so long as the first switch does not change from on to off and the second switch does not be switched on within the predetermined time period when the first switch changes from off to on, the predetermined time period being longer than a time period expected to be required for the depression button to move in a stroke from the first stage to the second stage; and a step of providing a second function of the endoscope without providing the first function regardless of a state of the first switch when the second switch is on.

Further, an endoscope system control method according to the present invention is an endoscope system control method for controlling an endoscope system including a two-stage depression button provided in an operation portion of an endoscope, a first switch disposed at a first stage depressing operation position in the depression button and configured so as to change from off to on by the first stage depressing operation and maintain an on state after the first stage, a second switch disposed at a second stage depressing operation position in the depression button and configured so as to change from off to on by the second stage depressing operation, the method having: a step of providing a first function of the endoscope with a delay of a predetermined time period so long as the first switch does not change from on to off and the second switch does not be switched on within the predetermined time period when the first switch changes from off to on, the predetermined time period being longer than a time period expected to be required for the depression button to move in a stroke from the first stage to the second stage; and a step of providing a second function of the endoscope without providing the first function regardless of a state of the first switch when the second switch is on.

An endoscope system according to the present invention includes: an n(n is an integer equal to or more than 2)-stage operating member provided in an operation portion of an endoscope; an mth switch disposed at an m(m is an integer equal to or more than 1 and less than n)th stage operation position in the operating member and configured so as to change from off to on by the mth stage operation and maintain an on state after the mth stage; an (m+1)th switch disposed at an (m+1)th stage operation position in the operating member and configured so as to change from off to on by the (m+1)th stage operation and maintain the on state only while the (m+1)th stage operation is maintained when m is (n−1) and maintain the on state after the (m+1)th stage when m is (n−2) or less; and control means which performs control so as to provide an mth function of the endoscope when the mth switch is on and provide an (m+1)th function of the endoscope without providing the mth function regardless of a state of the mth switch when the (m+1)th switch is on, the control means performing control so as to provide the mth function with a delay of a predetermined time period so long as the mth switch does not change from on to off within the predetermined time period when the mth switch changes from off to on, the predetermined time period being longer than a time period expected to be required for the operating member to move in a stroke from the mth stage to the (m+1)th stage.

BRIEF DESCRIPTION OF THE DRAWINGS

FIG. 6 is a sectional view schematically showing a configuration of the air feeding/water feeding button at a time when the first switch and the second switch are on in the above Embodiment 1;

FIG. 7 is a diagram showing a relationship between push-in strokes in depressing the air feeding/water feeding button and states of the first switch and the second switch in the above Embodiment 1;

FIG. 8 is a timing chart showing actions of electromagnetic valves in performing air feeding in the above Embodiment 1;

DETAILED DESCRIPTION OF THE PREFERRED EMBODIMENT(S)

In the following, an embodiment of the present invention will be described with reference to drawings.

Embodiment 1

Figure 1:
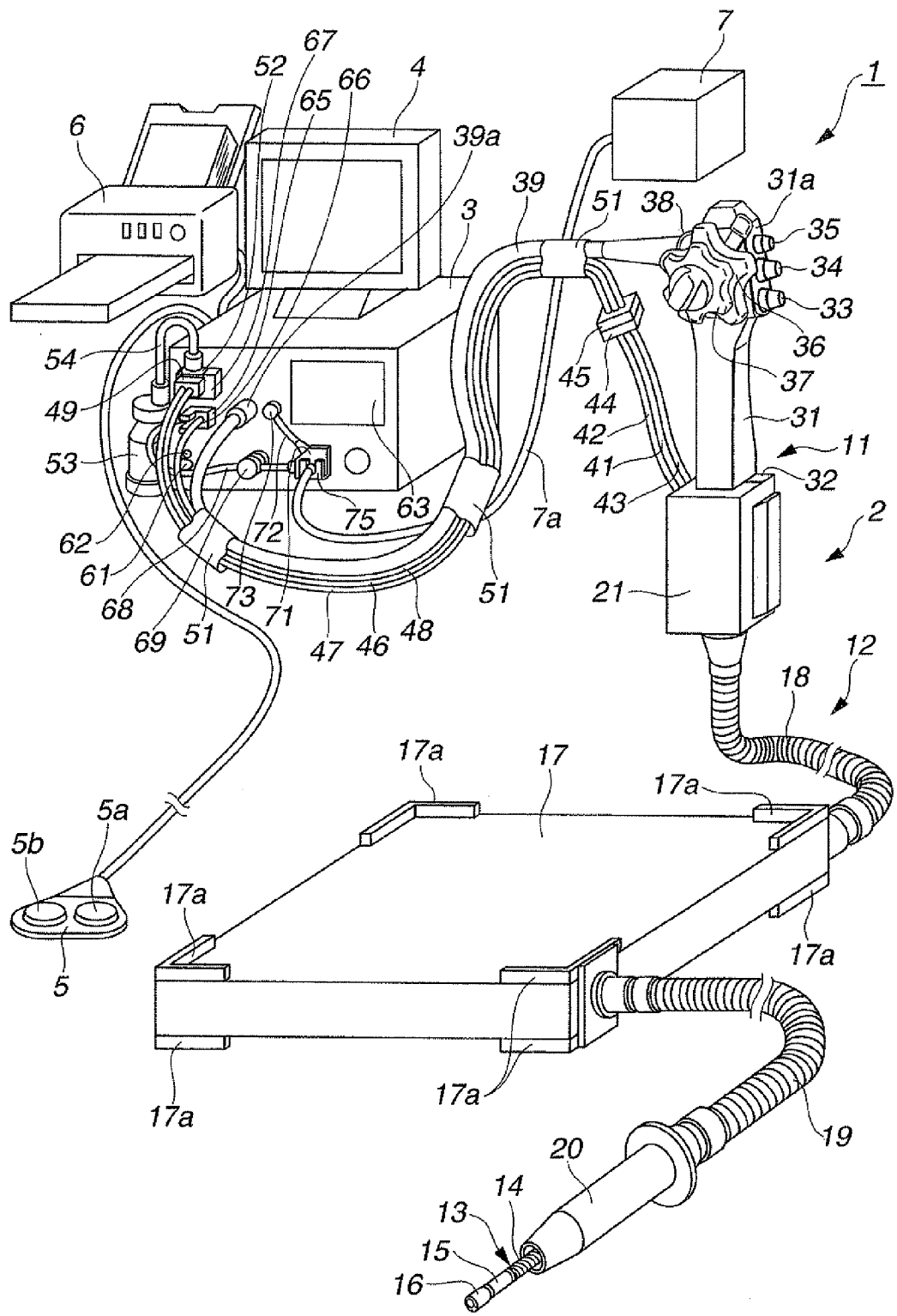
FIG. 1 is a view showing a configuration of a rotary self-propelled endoscope system in Embodiment 1 of the present invention.
Figure 2:
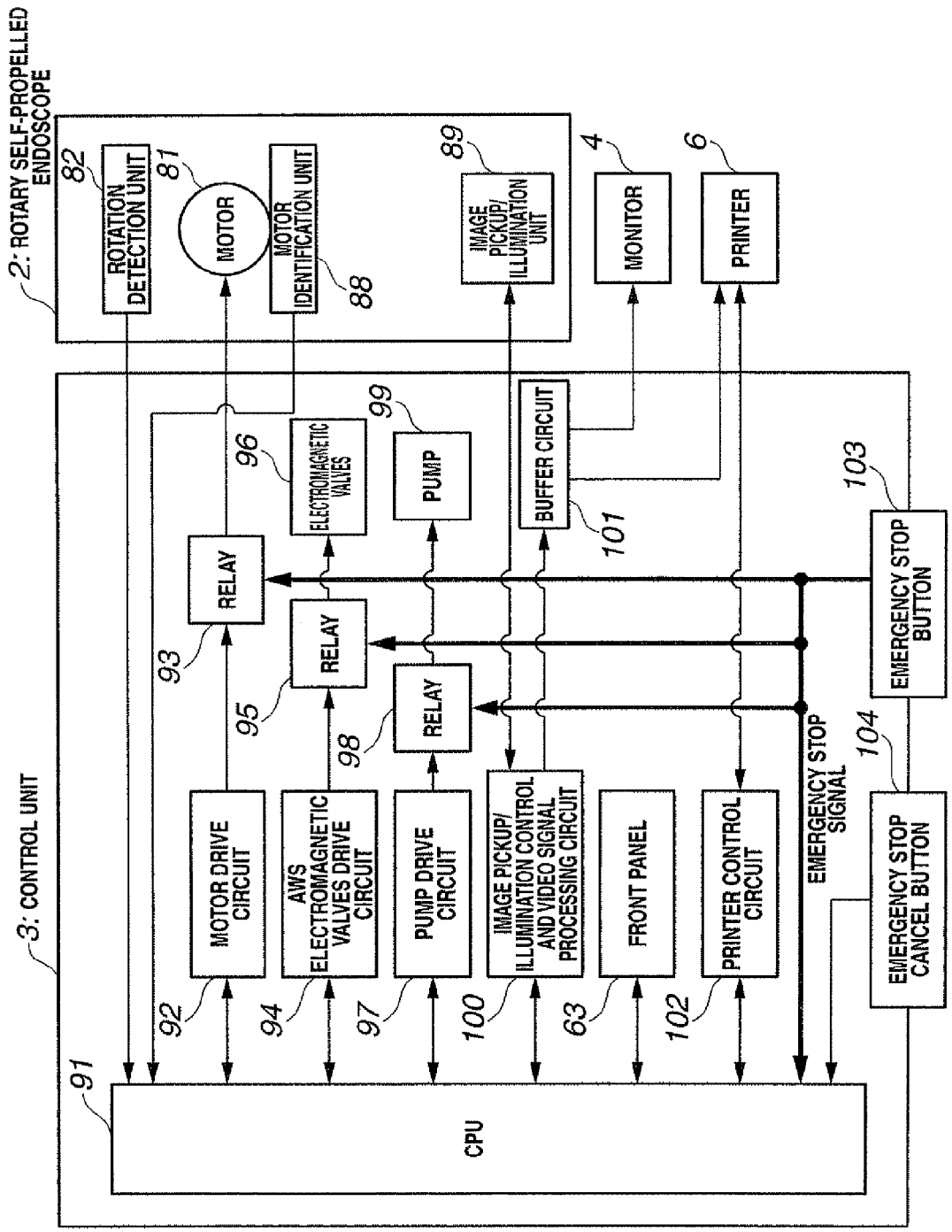
FIG. 2 is a block diagram showing an electrical configuration of the rotary self-propelled endoscope system in the above Embodiment 1.
Figure 3:
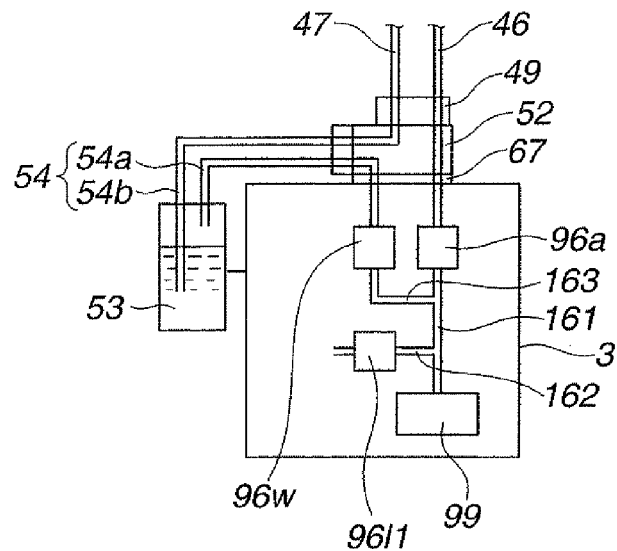
FIG. 3 is a view showing an example of a configuration of an air feeding and water feeding conduit line system in a control unit of the above Embodiment 1.
Figure 4:
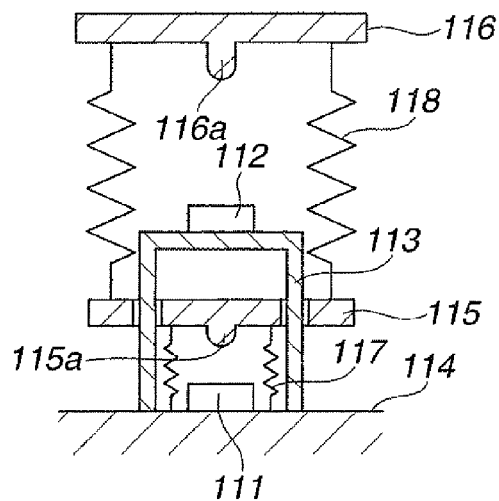
FIG. 4 is a sectional view schematically showing a configuration of an air feeding/water feeding button at a time when a first switch and a second switch are off in the above Embodiment 1.
Figure 5:
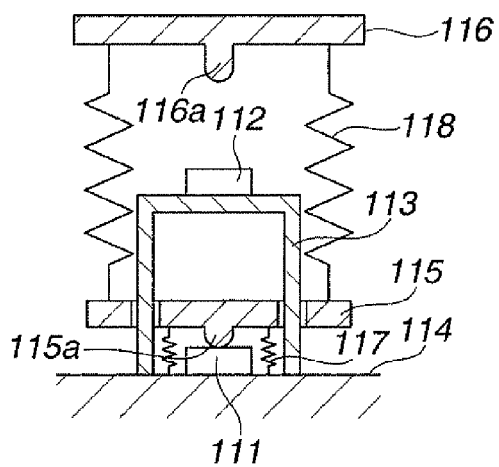
FIG. 5 is a sectional view schematically showing a configuration of the air feeding/water feeding button at a time when the first switch is on and the second switch is off in the above Embodiment 1.
Figure 9:
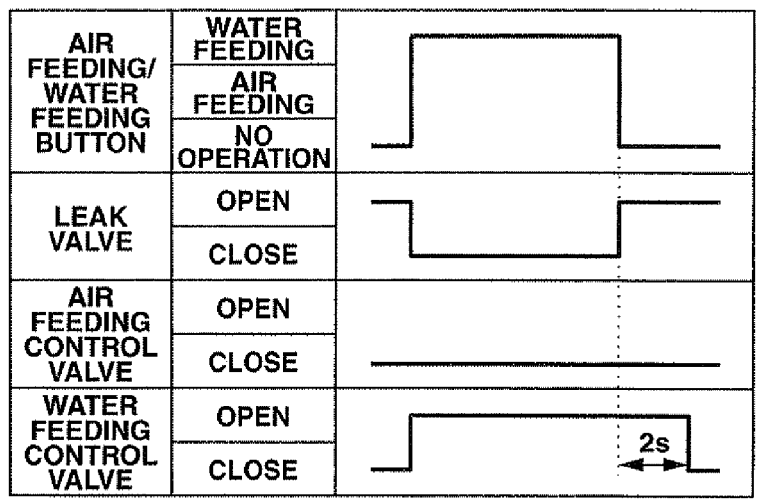
FIG. 9 is a timing chart showing actions of the electromagnetic valves in performing water feeding in the above Embodiment 1.
Figure 10:
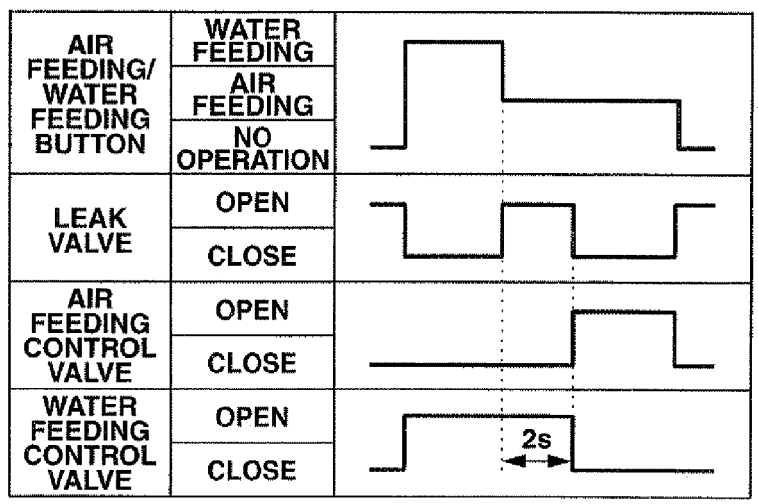
FIG. 10 is a timing chart showing actions of the electromagnetic valves in performing water feeding and thereafter performing air feeding.
Figure 11:
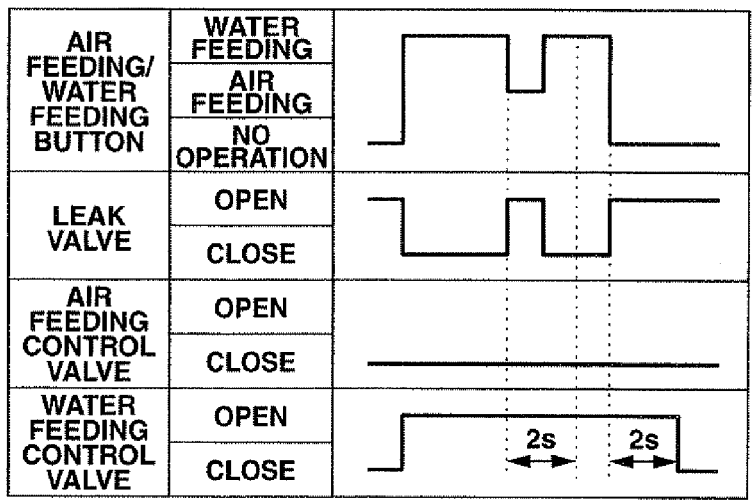
FIG. 11 is a timing chart showing actions of the electromagnetic valves in performing water feeding and thereafter again performing water feeding in the above Embodiment 1.
Figure 12:
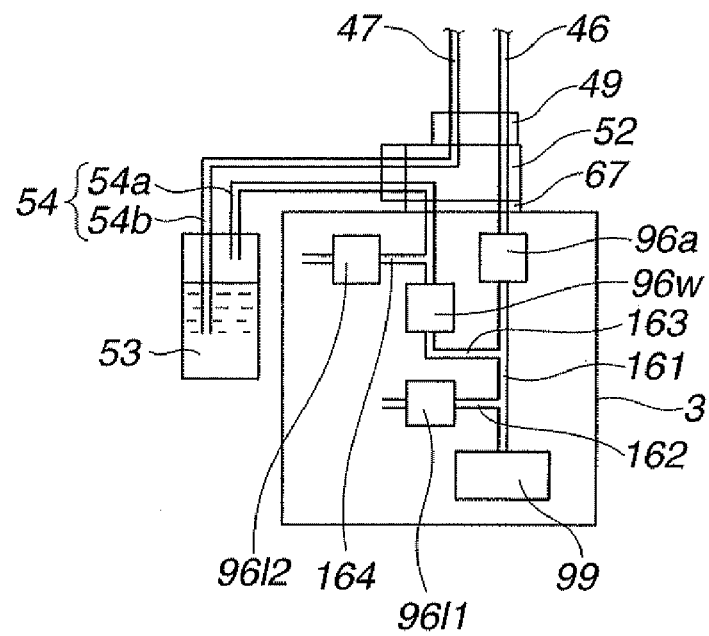
FIG. 12 is a view showing a first modification of the configuration of the air feeding and water feeding conduit line system in the control unit of the above Embodiment 1.
Figure 13:
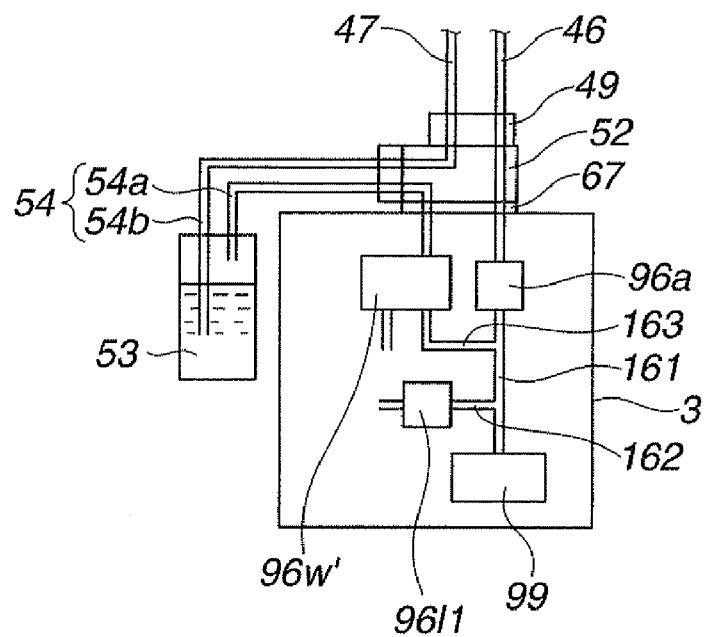
FIG. 13 is a view showing a second modification of the configuration of the air feeding and water feeding conduit line system in the control unit of the above Embodiment 1.

FIGS. 1 to 13 show Embodiment 1 of the present invention: FIG. 1 is a view showing a configuration of a rotary self-propelled endoscope system; FIG. 2 is a block diagram showing an electrical configuration of the rotary self-propelled endoscope system; FIG. 3 is a view showing an example of a configuration of an air feeding and water feeding conduit line system in a control unit; FIG. 4 is a sectional view schematically showing a configuration of an air feeding/water feeding button at a time when a first switch and a second switch are off; FIG. 5 is a sectional view schematically showing a configuration of the air feeding/water feeding button at a time when the first switch is on and the second switch is off; FIG. 6 is a sectional view schematically showing a configuration of the air feeding/water feeding button at a time when the first switch and the second switch are on; FIG. 7 is a diagram showing a relationship between push-in strokes in depressing the air feeding/water feeding button and states of the first switch and the second switch; FIG. 8 is a timing chart showing actions of electromagnetic valves in performing air feeding; FIG. 9 is a timing chart showing actions of the electromagnetic valves in performing water feeding; FIG. 10 is a timing chart showing actions of the electromagnetic valves in performing water feeding and thereafter performing air feeding; FIG. 11 is a timing chart showing actions of the electromagnetic valves in performing water feeding and thereafter again performing water feeding; FIG. 12 is a view showing a first modification of the configuration of the air feeding and water feeding conduit line system in the control unit; FIG. 13 is a view showing a second modification of the configuration of the air feeding and water feeding conduit line system in the control unit.

In the present embodiment, as an example of an endoscope system having a two-stage depression button for providing the function of an endoscope, a rotary self-propelled endoscope system is quoted which is a detachable-insertion-portion-type endoscope system. However, of course the detachable-insertion-portion-type endoscope system is not limited to the rotary self-propelled endoscope system but broadly includes detachable-insertion-portion types. In addition, the endoscope system having a two-stage depression button for providing function of an endoscope is not limited to the detachable-insertion-portion-type endoscope system, either.

First, with reference to FIG. 1, a configuration of a rotary self-propelled endoscope system will be described.

The rotary self-propelled endoscope system (hereinafter arbitrarily abbreviated as an endoscope system simply) 1 has a rotary self-propelled endoscope (hereinafter arbitrarily abbreviated as an endoscope simply) 2, a control unit 3, a monitor 4, a foot switch 5 and a printer 6.

The endoscope 2 has provided an elongated insertion portion 12 extending from an operation portion 11 which is in a hand side. The insertion portion 12 is configured including an insertion portion main body 13 which can be actually inserted into a subject and other portions described later which are for supporting the insertion portion main body 13. The insertion portion 12 is detachably attached to the operation portion 11 and is configured as disposable one which is discarded once used, for example.

On an outer peripheral side of the insertion portion main body 13, a rotating cylindrical body 14 having a spiral convex portion formed on an outer peripheral surface is provided so as to be rotatable about an insertion axis.

On a distal end side of the rotating cylindrical body 14 in the insertion portion main body 13, a bending portion 15 is provided which is freely bendable. The distal end of the rotating cylindrical body 14 abuts on an abutting portion on a proximal end side of the bending portion 15 so as to transmit propelling force generated by rotation.

On a most distal end side of the insertion portion main body 13 provided adjacent to the bending portion 15, a distal end rigid portion 16 is provided. The distal end rigid portion 16 has disposed an image pickup/illumination unit 89 (see FIG. 2) described later, an air feeding nozzle, a water feeding nozzle, a suction port and the like.

When being unused and when having been used, such insertion portion main body 13 is accommodated in most part thereof in an accommodating case 17 which is a component of the insertion portion 12. The accommodating case 17 is a box in a form of a rectangular parallelepiped close to a flat plate, for example, and can be put with either of principal surfaces up or down, leg portions 17a for putting being provided at four corners of each principal surface. The accommodating case 17 is configured such that a height of an inner side is slightly greater than a diameter of the rotating cylindrical body 14 and less than two times the diameter of the rotating cylindrical body 14. Thereby, the accommodating case 17 prevents the insertion portion main body 13 from being kinked to wriggle by rotational force applied to the rotating cylindrical body 14. That is, if the insertion portion main body 13 were kinked to wriggle, rotational force would be consumed for kinking so as not to be transmitted sufficiently as force for propulsion.

For similar reasons, a section from the accommodating case 17 to the operation portion 11 and a predetermined length from the accommodating case 17 to the distal end side are respectively protected by an operation portion side guide tube 18 which is a component of the insertion portion 12 and a distal end side guide tube 19 which is a component of the insertion portion 12 while being prevented from kinking to wriggle.

In the distal end side beyond the distal end side guide tube 19, an insertion aid 20 (which is also a portion of the insertion portion 12) used upon insertion into a subject is provided by being loosely fitted on the outer periphery of the insertion portion main body 13. The rotary self-propelled endoscope system 1 is contemplated for use upon automatic insertion of the endoscope 2 through an anus into a large intestine or the like, for example. The insertion aid 20 is for enabling smooth insertion while protecting an anal portion on that occasion.

In addition, on the hand side of the insertion portion 12, a connector portion 21 for connecting with a motor box 32 described later of the operation portion 11 is provided.

Meanwhile, the operation portion 11 has a grip portion 31 provided with various operating buttons and the like in a head portion 31a as well as a motor box 32 provided adjacent to the grip portion 31 on the distal end side thereof.

The motor box 32 contains a motor 81 (see FIG. 2) as a driving source for driving the rotating cylindrical body 14. An unshown bending wire for bending the above-described bending portion 15 is also connected to a driving mechanism in a later-described bending knob side via connection of the motor box 32 and the connector portion 21. Rotational driving force from the motor 81 is transmitted on some one region (or whole) of the rotating cylindrical body 14 to rotate the rotating cylindrical body 14. Therefore, the region of transmission may be whichever of a proximal end side, the distal end side and midway of the rotating cylindrical body 14.

Further, signal lines to the image pickup/illumination unit 89 and the like are also electrically connected with signal lines to the control unit 3 side via connection of the motor box 32 and the connector portion 21.

In the head portion 31a of the grip portion 31 to grasp with a hand, there are provided an air feeding/water feeding button 33 for performing air feeding and water feeding, a suction button 34 for performing suction, an image pickup button 35 for picking up still images, a U/D bending knob 36 for bending the above-described bending portion 15 in an up (U) or down (D) direction in an observed image, an R/L bending knob 37 for bending the bending portion 15 in a right (R) or left (L) direction in an observed image, a rotary operating lever 38 for operating advance/stop/retreat of the rotating cylindrical body 14 and the like.

An electric cable 39 for performing transmission of signals between the image pickup/illumination unit 89 and the control unit 3 is provided extending from the head portion 31a of the grip portion 31, and a connector 39a provided on a distal end side thereof is connected to a connector receptacle on the control unit 3.

From the connector portion 21 on the hand side of the insertion portion 12, an air feeding tube 41, a water feeding tube 42 and a suction tube 43 are extending out which are disposed in the insertion portion main body 13. A connector 44 is provided on a proximal end side of these tubes.

The connector 44 is detachably connected with a connector 45 provided on a distal end side of an air feeding relay tube 46, a water feeding relay tube 47 and a suction relay tube 48. At a time of connection, an air feeding tube 41 with an air feeding relay tube 46, a water feeding tube 42 with a water feeding relay tube 47, and a suction tube 43 with a suction relay tube 48 are respectively caused to communicate.

Here, the air feeding tube 41, water feeding tube 42 and suction tube 43 as well as the air feeding relay tube 46, water feeding relay tube 47 and suction relay tube 48 described above are also portions of the disposable insertion portion 12.

The air feeding relay tube 46, water feeding relay tube 47 and suction relay tube 48 are detachably fixed to the electric cable 39 with one or a plurality of temporary fixture(s) 51 (three in an example shown in FIG. 1). The fixation of the air feeding relay tube 46, water feeding relay tube 47 and suction relay tube 48 to the electric cable 39 eliminates each one's drooping or the like, thereby facilitating handling of the endoscope 2.

The relay tubes 46 to 48 described above have their proximal end sides connected to the control unit 3. Here, the control unit 3 is for performing control of the image pickup/illumination unit 89, control of air feeding/water feeding/ suction, control of the motor 81 and the like, as described later, and is to be attached on a side surface with a water feeding tank 53 used for air feeding/water feeding.

More particularly, the suction relay tube 48 has the proximal end side connected to an insertion portion side suction connecting portion 66 of the control unit 3. Here, the insertion portion side suction connecting portion 66 is detachably attached to an insertion portion side suction connecting portion retaining member 65 fixed to a surface of the control unit 3. On the proximal end side of the air feeding relay tube 46 and water feeding relay tube 47, there is provided an air feeding and water feeding ferrule 49 which is connected via an air feeding and water feeding connector 52 to an air feeding and water feeding connector connecting portion 67 provided on the control unit 3. Here, the air feeding and water feeding connector 52 is configured as an independent member which is connected to the air feeding and water feeding connector connecting portion 67, and to which are further connected the above-described air feeding and water feeding ferrule 49 and a water feeding tube 54 provided extending from the water feeding tank 53.

The above-described insertion portion side suction connecting portion 66 is provided on one end of an insertion portion side suction tube 68. The insertion portion side suction tube 68 is pinched in a pinch valve 69 provided on a front surface of the control unit 3 and thereafter is connected to a branch portion 71. From the branch portion 71, a leak side tube 72 branches which is connected via a connecting portion 73 provided on a distal end thereof to a leak conduit line in the control unit 3.

The above-described insertion portion side suction connecting portion 66, insertion portion side suction tube 68, branch portion 71, leak side tube 72 and connecting portion 73 are configured as integral members assembled in advance, among which the branch portion 71 is locked in a locking portion 75 provided on the control unit 3 to be detachably fixed.

A suction device connecting ferrule is provided on the branch portion 71 such that a distal end of a suction device side suction tube 7a is connected which is provided extending from a suction device 7. For the suction device 7, one equipped in a hospital or the like can be used, for example. However, the suction device 7 may, of course, be provided in the rotary self-propelled endoscope system 1 itself as a part of a system configuration.

In the control unit 3, there are provided a power source switch 61, an LED 62 which indicates a state of a power source, a front panel 63 for performing various operations and the like. Here, the front panel 63 is configured including a standby switch, a switch for controlling rotation of the rotating cylindrical body 14 and the like.

A foot switch 5 is detachably connected to the control unit 3 and is configured having an advance button 5a for advancing the rotating cylindrical body 14 and a retreat button 5b for retreating the rotating cylindrical body 14. Although the foot switch 5 is used for controlling rotation of the rotating cylindrical body 14 here, the same may be used for other purposes as well.

Thus, rotational states of the rotating cylindrical body 14 can be operated by using whichever of the rotary operating lever 38 of the operation portion 11, the foot switch 5 and the control unit 3.

The monitor 4, detachably connected to the control unit 3, displays a monitor image being picked up by the image pickup/illumination unit 89 as well as displays various information such as rotational states of the rotating cylindrical body 14 and states of torque required for rotation of the rotating cylindrical body 14.

The printer 6 is detachably connected to the control unit 3 and prints out a still image based on control of the control unit 3 when the image pickup button 35 of the endoscope 2 is depressed.

Next, with reference to FIG. 2, an electrical configuration of the rotary self-propelled endoscope system 1 will be described.

The control unit 3 has a CPU 91, a motor drive circuit 92, a relay 93, an AWS electromagnetic valves drive circuit 94, a relay 95, electromagnetic valves 96, a pump drive circuit 97, a relay 98, a pump 99, an image pickup/illumination control and video signal processing circuit 100, a buffer circuit 101, the front panel 63, a printer control circuit 102, an emergency stop button 103 and an emergency stop cancel button 104.

In addition, the endoscope 2 has the motor 81, a rotation detection unit 82, a motor identification unit 88 and the image pickup/illumination unit 89.

The CPU 91 is control means for overall control of the rotary self-propelled endoscope system 1 and also serves as drive control means for performing drive control of the motor 81 via the motor drive circuit 92.

The motor drive circuit 92 is drive control means connected to the motor 81 via the relay 93 for performing drive control of the motor 81 based on control of the CPU 91 which executes a predetermined control program. In addition, the motor drive circuit 92 also serves as current detecting means which detects current value driving the motor 81 and outputs the detected value to the CPU 91 as needed. When the detected value reaches a predetermined upper limit current value Imax, the CPU 91 performs control such that the drive of the motor 81 is automatically stopped, thereby obtaining security.

The rotation detection unit 82 is for detecting rotation rates of the motor 81, wherein detection results are outputted to the CPU 91. The CPU 91 performs control such as constant speed drive of the motor 81 based on rotation rates detected by the rotation detection unit 82.

The motor identification unit 88 outputs to the CPU 91 motor identification information which indicates a kind of the motor 81 contained in the endoscope 2. The endoscope 2 is considered to contain different kinds of motors 81 as a drive source, wherein different kinds of motors 81 have different drive methods. Therefore, the CPU 91 obtains from the motor identification unit 88 the kind of the motor 81 contained in the endoscope 2 connected, and controls the motor drive circuit 92 so as to cause the same to perform a drive according to that kind. The motor identification unit 88 may actively output a motor identification signal when the endoscope 2 and the control unit 3 are connected, as well as may be a non-volatile memory or the like which is passively read by the CPU 91 of motor identification information.

The AWS electromagnetic valves drive circuit 94 drives the electromagnetic valves 96 for controlling air feeding (A), water feeding (W) and suction (S) via the relay 95 based on control of the CPU 91.

The pump drive circuit 97 drives the pump 99 via the relay 98 based on control of the CPU 91. The pump 99 is a pump used for air feeding/water feeding.

The image pickup/illumination control and video signal processing circuit 100, being connected with the image pickup/illumination unit 89 and based on control of the CPU 91, supplies power for illumination to the illumination unit supplies drive clocks and the like to the image pickup unit, and further performs various video signal processing on video signals outputted from the image pickup unit.

The image pickup/illumination control and video signal processing circuit 100 is connected to the buffer circuit 101, which is connected to the monitor 4 and further connected to the printer 6. As described above, a still image is recorded when the image pickup button 35 of the operation portion 11 is depressed. A stoppage of the observed image displayed on the monitor 4 at this time would be inconvenient for performing a procedure. That is why the monitor 4 and the printer 6 are connected to observation-purpose video output and to image-recording-purpose video output respectively. Thereby, when the printer 6 prints out a still image upon depression of the image pickup button 35, a moving image can continue to be observed on the monitor 4.

The front panel 63 is operating input means configured by arranging various switches, LEDs and the like, wherein operation signals are outputted to the CPU 91 upon button operation and the like. The front panel 63 includes a standby switch. Upon depression of the standby switch, control signals are sent from the CPU 91 all at once to the motor drive circuit 92, the AWS electromagnetic valves drive circuit 94, a pump control circuit and the image pickup/illumination control and video signal processing circuit 100, thereby effecting stopping of the motor 81, stopping of drive power source supply to the electromagnetic valves 96 for AWS, stopping of the pump 99 and stopping of power source supply to the image pickup/illumination unit 89. Since the pinch valve 69 opens in this state, replacement of the insertion portion side suction tube 68 can be performed as described later. When the standby switch is depressed again after the insertion portion side suction tube 68 is replaced, each of the stopped functions is restored to an original action state.

The printer control circuit 102 controls action of the printer 6 based on control of the CPU 91. For example, when the image pickup button 35 provided in the operation portion 11 of the endoscope 2 is depressed, the printer control circuit 102 controls the printer 6 such that a still image accumulated in the buffer circuit 101 is printed.

The emergency stop button 103, connected to the CPU 91 and the relays 93, 95, 98, is an operating button for setting an emergency stop mode. As described above, the CPU 91 detects drive current value of the motor 81 and performs control such that the drive of the motor 81 is automatically stopped when the detected value reaches the upper limit current value Imax. The endoscope system 1, further provided with the emergency stop button 103, is configured such that an emergency stop of various actions can be manually performed. That is, when the emergency stop button 103 is depressed, an emergency stop signal is sent out and the CPU 91 in any situation recognizes it as an emergency state and stops each of the motor drive circuit 92, the AWS electromagnetic valves drive circuit 94 and the pump drive circuit 97. Meanwhile, the emergency stop signal from the emergency stop button 103 is directly outputted to the relays 93, 95, 98, thereby breaking electrical connection between the motor drive circuit 92 and the motor 81, breaking electrical connection between the AWS electromagnetic valves drive circuit 94 and the electromagnetic valves 96, and breaking electrical connection between the pump drive circuit 97 and the pump 99. However, electrical connection between the image pickup/illumination control and video signal processing circuit 100 and the image pickup/illumination unit 89 is not broken since that is necessary thereafter for withdrawing the endoscope 2 safely or performing a procedure.

The emergency stop cancel button 104 is an operating button for canceling the emergency stop mode set by the above-described emergency stop button 103, configured so as to provide its function by being held depressed for a long interval. The emergency stop cancel button 104 is configured such that the same has to be held depressed for a long interval in order to cancel the emergency stop mode; this is for a purpose of confirming a notion of an operator that he/she has eliminated a factor which caused him/her to perform the emergency stop.

Next, with reference to FIG. 3, a configuration of an air feeding and water feeding conduit line system in the control unit 3 will be described.

The air feeding relay tube 46 is connected via the air feeding and water feeding ferrule 49, the air feeding and water feeding connector 52 and the air feeding and water feeding connector connecting portion 67 to an air feeding conduit line 161 in the control unit 3, and is connected to the pump 99 for pressurizing air. On the air feeding conduit line 161 in the control unit 3, an air feeding control valve 96a is disposed which is one of the electromagnetic valves 96.

The water feeding relay tube 47 is connected via the air feeding and water feeding ferrule 49 and the air feeding and water feeding connector 52 to the water feeding tube 54. In the water feeding tube 54, a water feeding tank air feeding conduit line 54a and a water feeding conduit line 54b are disposed; the water feeding relay tube 47 is, more particularly, in communication with the water feeding conduit line 54b. A distal end of the water feeding conduit line 54b reaches a position under water in the water feeding tank 53. On the other hand, the water feeding tank air feeding conduit line 54a is disposed such that its distal end is in an air part in the water feeding tank 53 (that is, in a position higher in a direction of gravity than a full water level of the water feeding tank 53). The water feeding tank air feeding conduit line 54a is, via the air feeding and water feeding connector 52 and the air feeding and water feeding connector connecting portion 67, in communication with a water feeding tank air feeding conduit line 163 in the control unit 3. The water feeding tank air feeding conduit line 163 branches between the pump 99 and the air feeding control valve 96a from the air feeding conduit line 161 in the control unit 3. On the water feeding tank air feeding conduit line 163 in the control unit 3, a water feeding control valve 96w is provided which is one of the electromagnetic valves 96.

In addition, from between the pump 99 and the air feeding control valve 96a in the air feeding conduit line 161, a leak conduit line 162 branches, on which a leak valve 9611 is provided which is one of the electromagnetic valves 96. Thereby, the air feeding conduit line 161 is in communication with an outer atmosphere via the leak valve 9611.

The above-described electromagnetic valves 96 act independently of each other; the actions will be described later with reference to FIGS. 8 to 11.

Next, with reference to FIGS. 4 to 6, a configuration of the air feeding/water feeding button 33 will be described. In FIGS. 4 to 6, downward directions of the drawings are inward directions of the operation portion 11, and upward directions of the drawings are outward directions of the operation portion 11.

The air feeding/water feeding button 33 being an operating member is, as a depression button enabling two-stage operation by means of push-in strokes, configured as described below, for example.

A first switch 111 is fixed to an operation portion main body 114 in the operation portion 11. The first switch 111 is configured by a contact switch, for example.

The first switch 111 is depressed by a first movable member 115 arranged above, on which a depressor portion 111a for depressing the first switch 111 is formed.

The first movable member 115 is movable in an up-and-down direction with respect to the operation portion main body 114, and is joined to the operation portion main body 114 through a first spring 117.

In addition, above the first switch 111, a second switch 112 is provided which is fixed to the operation portion main body 114 through a fixing member 113. The second switch 112 as well as the first switch 111 is configured by a contact switch, for example.

The second switch 112 is depressed by a second movable member 116 arranged above, on which a depressor portion 116a for depressing the second switch 112 is formed.

The second movable member 116 is movable in the up-and-down direction with respect to the operation portion main body 114 and the first movable member 115, as well as is joined to the first movable member 115 through a second spring 118. Here, configuration is such that a spring constant of the second spring 118 is larger than a spring constant of the first spring 117.

Next, effects of the thus configured air feeding/water feeding button 33 will be described.

First, FIG. 4 shows appearance of the air feeding/water feeding button 33 when depression is not performed. At this time, there is a first predetermined interval between the first switch 111 and the depressor portion 115a, and between the second switch 112 and the depressor portion 116a there is a second predetermined interval longer than the first predetermined interval. Therefore, both the first switch 111 and the second switch 112 are off.

Next, when the second movable member 116 is depressed downward, at first mainly the first spring 117 is compressed, since the spring constant of the second spring 118 is greater than the spring constant of the first spring 117. Then, the first movable member 115 and the second movable member 116 move substantially integrally downward. Thereafter, when they have moved to a first stage depressing operation position shown in FIG. 5, the depressor portion 115a abuts on the first switch 111 and the first switch 111 is switched on. At this time, however, the second switch 112 remains off.

Next, when the second movable member 116 is further depressed downward, the second spring 118 is compressed since the first movable member 115 is configured such that the same can not move downward beyond an unshown abutting portion or the like. Then, when it has moved to a second stage depressing operation position shown in FIG. 6, the depressor portion 116a abuts on the second switch 112 and the second switch 112 is switched on. Therefore, at this time, both the first switch 111 and the second switch 112 are on.

On the other hand, when the depression of the air feeding/water feeding button 33 is quitted, first the second switch 112 is switched off and thereafter the first switch 111 is switched off, which is reverse to an order described above.

Next, with reference to FIG. 7, relation of push-in strokes to states of the first switch and the second switch during depression of the above-described air feeding/water feeding button 33 will be described.

After a start of depression of the air feeding/water feeding button 33, when the same has been pushed in to a stroke S1, a state shown in FIG. 5 is entered, where the first switch 111 is changed from off to on. At this time, the second switch 112 remains off as described above.

Further, in continuation of the depression of the air feeding/water feeding button 33, when the same has been pushed in to a stroke S2, a state shown in FIG. 6 is entered, where the second switch 112 is changed from off to on. Therefore at this time, both the first switch 111 and the second switch 112 are on.

Immediately after the depression to the stroke S2, the second movable member 116 abuts on an unshown abutting portion or the like to reach a maximum stroke Smax, where no further depressing operation can be performed.

On the other hand, as depressing force on the air feeding/water feeding button 33 is reduced (or depressing force ceases to be applied; hereinafter represented by description "depressing force is reduced"), the push-in stroke decreases at first mainly by a biasing force of the second spring 118, and when the stroke has returned to S2, the second switch 112 is changed from on to off.

As the depressing force on the air feeding/water feeding button 33 is further reduced, only the second movable member 116 moves upward by the biasing force of the second spring 118 so that the push-in stroke decreases. Then, a little short of the stroke S1 (at a position a little away from the stroke S1 toward the stroke S2), the first movable member 115 and the second movable member 116 start to move substantially integrally, at this time mainly by a biasing force of the first spring 117. The push-in stroke thus decreases to return to the stroke S1, where the first switch 111 is changed from on to off.

Thereafter, with the first switch 111 and the second switch 112 being off; the stroke returns from S1 to 0.

Next, with reference to FIGS. 8 to 11, timing of operations and control timing of the electromagnetic valves in operation of the above-described air feeding/water feeding button 33 will be described.

First, FIG. 8 shows actions of the electromagnetic valves in performing air feeding.

When depressing operation of the air feeding/water feeding button 33 is not performed (in a no operation state), the CPU 91, through the AWS electromagnetic valves drive circuit 94, opens only the leak valve 9611 and closes the air feeding control valve 96a and the water feeding control valve 96w. Thereby, air feeding from the pump 99 is leaking via the leak valve 9611 to an exterior.

Next, when the air feeding/water feeding button 33 is operated and depressed until reaching the stroke S1, only the first switch 111 is switched on. Then, after a delay of a predetermined time period, for example, 0.3 second, the CPU 91 opens the air feeding control valve 96a and closes the leak valve 9611 through the AWS electromagnetic valves drive circuit 94. Thereby, air feeding from the pump 99 is fed to the air feeding relay tube 46 and further via the air feeding tube 41, air feeding is performed from the air feeding nozzle of the distal end rigid portion 16.

Thereafter, if the depressing force on the air feeding/water feeding button 33 is reduced to operate such that the stroke becomes less than S1, the first switch 111 is changed to off. The CPU 91, at this time without a delay, opens the leak valve 9611 and closes the air feeding control valve 96a through the AWS electromagnetic valves drive circuit 94. Thereby, a state is entered in which air feeding from the pump 99 is leaking via the leak valve 9611 to the exterior.

Next, FIG. 9 shows actions of the electromagnetic valves in performing water feeding.

When the air feeding/water feeding button 33 is in the no operation state, air feeding from the pump 99 is leaking via the leak valve 9611 to the exterior, in a same way as described above.

Next, the air feeding/water feeding button 33 is operated to be depressed until reaching the stroke S2 via the stroke S1.

At this time, only the first switch 111 is in an on state during a short time period in which the stroke moves from S1 to S2, even if the air feeding/water feeding button 33 is pushed in at a stretch. However, as described with FIG. 8, the air feeding control valve 96a opens 0.3 second after only the first switch 111 is switched on. If the second switch 112 is switched on in the 0.3 second, air feeding is not performed and only water feeding is performed.

When a typical operator pushes in the air feeding/water feeding button 33 in order to perform water feeding, a time period required for the stroke to move from S1 to S2 is thought to be about 0.1 to 0.2 second, for example. Thus, in air feeding, the above-described 0.3 second has been set as a predetermined time period longer than the time period expected to be required for the stroke movement. Thus, by providing the delay of 0.3 second, it is prevented that air feeding should be performed for a short time period immediately before water feeding when the button is operated for water feeding. Although 0.3 second is set as the predetermined delay time here, it is not limited thereto. A configuration may be such that an operator can set a desired delay time by operating the front panel 63 or the like, for example, considering a speed by which he/she operates the button.

When the stroke thus reaches S2 without performing air feeding, the second switch 112 is switched on and at this time water feeding is performed without a delay. That is, when the second switch 112 is switched on, the water feeding control valve 96w opens and the leak valve 9611 closes. Thereby, air feeding from the pump 99 is fed via the water feeding control valve 96w to the water feeding tank air feeding conduit line 54a. Then air pressure in the water feeding tank 53 increases to depress a water surface. By the pressure, water is fed from the water feeding conduit line 54b to the water feeding relay tube conduit line 47 and further via the water feeding tube 42, water feeding is performed from the water feeding nozzle of the distal end rigid portion 16. Therefore, during water feeding, the pressure in the water feeding tank 53 is in a state of being higher than atmospheric pressure.

Thereafter, when the depressing force of the air feeding/water feeding button 33 is reduced to operate such that the stroke becomes less than S1 via S2, first the second switch 112 is changed to off and then the first switch 111 is changed to off. Also at this time, air feeding action is not performed midway since the air feeding action is provided with a delay of 0.3 second, as described above. In addition, at this time, control is performed such that the air feeding action can not be performed for 2 seconds, as will be next explained.

That is, at a time point when the second switch 112 is switched off, the CPU 91 first opens the leak valve 9611. Next, the CPU 91 closes the water feeding control valve 96w after a delay of a predetermined time period, for example 2 seconds. For the 2 seconds the air feeding control valve 96a remains closed. That is, for 2 seconds after the second switch 112 is changed to off, the leak valve 9611 is open and the water feeding control valve 96w is open. Thereby, the water feeding tank air feeding conduit line 54a and an interior of the water feeding tank 53 are released under atmospheric pressure. When 2 seconds have elapsed after the second switch 112 is switched off, the water feeding tank air feeding conduit line 54a and the interior of the water feeding tank 53 being substantially under atmospheric pressure, the water feeding control valve 96w is closed. Thereafter again operations such as air feeding are possible.

Although the time period of release of the water feeding tank 53 to the atmosphere after water feeding is 2 seconds here, of course it is not limited thereto, and other suitable predetermined time periods can also be set.

Next, FIG. 10 shows actions of the electromagnetic valves in a case where water feeding is performed and thereafter air feeding is performed.

When the air feeding/water feeding button 33 is in the no operation state, air feeding from the pump 99 is leaking via the leak valve 9611 to the exterior, in a same way as described above.

Then, when the air feeding/water feeding button 33 is depressed until reaching the stroke S2, the second switch 112 is switched on to open the water feeding control valve 96w and close the leak valve 9611, thereby starting a water feeding action. At this time, an air feeding action is not performed midway in the depressing operation for a reason described above.

Thereafter, when the air feeding/water feeding button 33 is returned to the stroke St, the second switch 112 is switched off and only the first switch 111 is on. However at this time, in a same way as described above, the water feeding control valve 96w continues to remain open for 2 seconds, and also the leak valve 9611 is opened.

When 2 seconds have elapsed, the water feeding control valve 96w closes, the air feeding control valve 96a opens and the leak valve 9611 closes. At this time point, since 2 seconds have elapsed with only the first switch 111 being on and the above-described 0.3 second delay time has already elapsed, an air feeding action is immediately started.

Thereafter, when the first switch 111 is switched off and the air feeding/water feeding button 33 enters the no operation state, the leak valve 9611 opens and the air feeding control valve 96a closes to return to a leaking state.

Next, FIG. 11 shows actions of the electromagnetic valves in a case where water feeding is performed and thereafter again water feeding is performed.

When the air feeding/water feeding button 33 is in the no operation state, there is a leaking state.

Then, when the air feeding/water feeding button 33 is depressed until reaching the stroke S2, the second switch 112 is switched on to open the water feeding control valve 96w and close the leak valve 9611, thereby starting a water feeding action. Also at this time, an air feeding action is not performed midway in the depressing operation for the reason described above.

Thereafter, when the air feeding/water feeding button 33 is returned to the stroke S1, the second switch 112 is switched off and only the first switch 111 is on. However at this time, in a same way as described above, the water feeding control valve 96w continues to remain open until 2 seconds have elapsed, and also the leak valve 9611 opens.

Assume that when the state of the stroke S1 has continued for about 1 second, the air feeding/water feeding button 33 is again depressed until reaching the stroke S2. Then, since the above-described 2 seconds have not elapsed yet, only the leak valve 9611 closes, the air feeding control valve 96a having never been opened. At this time, the water feeding control valve 96w continues to remain open.

Water feeding is thus performed and thereafter, when the air feeding/water feeding button 33 returns from the second stage to the no operation state, the leak valve 9611 opens without undergoing any air feeding state as described above.

When 2 seconds have elapsed and release of the water feeding tank 53 to the atmosphere has been performed, the water feeding control valve 96w closes to return to the leaking state in the no operation time.

In the above description, the air feeding/water feeding button 33 functions to perform air feeding by the first stage depression and perform water feeding by the second stage depression. But even if it functions to perform water feeding by the first stage depression and perform air feeding by the second stage depression, which is reverse to above, unexpected performance of the first stage operation can be prevented when the button is operated with an intent to perform only the second stage operation. In that case, a start of a water feeding action is delayed by, for example, 0.3 second from when the first switch 111 is switched on by the first stage depression. In addition, a start of a water feeding action may be delayed by, for example, 0.3 second also from when the second switch 112 is changed from on to off.

Although as an example of a two-stage depression button a button is quoted here which provides air feeding function and water feeding function, it is not limited thereto. It may be any button which provides an appropriate first function of an endoscope by the first stage depression and an appropriate second function of the endoscope by the second stage depression, respectively.

Further, although in the above description the two-stage depression button is quoted as an example, it is not limited to two stages but may also be of three or more multiple stages. In addition, it is not limited to a depression-type operating member but may also be a multistage slide-type operating member, for example. The present invention can be widely applied to any one which is of multiple stages without being limited by a type of operation.

Although explanation is made with the rotary self-propelled endoscope system as an example in the above description, the present invention is not limited thereto but can be widely applied to endoscope systems having a multistage depression operating button (for example, an air feeding/water feeding button) configured to use an electric switch. Therefore, it is not limited to a detachable-insertion-portion-type endoscope system, either.

According to such Embodiment 1, a predetermined delay time is provided between the switching on of the first switch and the start of air feeding. Accordingly, unintended air feeding is not performed in a case where an operator pushes in the two-stage air feeding/water feeding button at a stretch for water feeding. Thus only water feeding can be started as intended.

Then, to stop water feeding, the water feeding control valve is closed after internal pressure of the water feeding tank is released to the atmosphere. Accordingly, water is not pushed out by residual pressure in the water feeding tank so that water is quickly stopped to enable observation of an object immediately after water feeding.

Further, since the leak valve is provided at a position where pressure of the pump can be directly let out, if the air feeding control valve or the water feeding control valve should be broken during air feeding or water feeding to be continuously open, the leak valve can be opened by stopping air feeding operation or water feeding operation. Thereby pressure of the pump is let out through the leak conduit line, so that a situation does not occur in which air feeding does not stop and a situation does not occur in which water feeding does not stop. Therefore, even further security can be obtained.

Next, with reference to FIG. 12, a first modification of the configuration of the air feeding and water feeding conduit line system in the control unit 3 will be described.

In the first modification shown in FIG. 12, in addition to the configuration shown in FIG. 3, a water feeding tank leak conduit line 164 is provided branching on the water feeding tank air feeding conduit line 163 in a water feeding tank 53 side with respect to the water feeding control valve 96w of the control unit 3. Further, on the water feeding tank leak conduit line 164, a water feeding tank leak valve 9612 is provided which is dedicated to releasing the internal pressure of the water feeding tank 53.

To perform water feeding in such a configuration, the water feeding tank leak valve 9612 is closed and the water feeding control valve 96w is opened to pressurize the water feeding tank 53, and water feeding is performed.

Then, to stop water feeding, the water feeding control valve 96w is closed and the water feeding tank leak valve 9612 is opened. Thereby, the residual pressure in the water feeding tank 53 is released from the water feeding tank leak valve 9612 to the atmosphere to lower the internal pressure of the water feeding tank 53 to approximately atmospheric pressure.

According to such first modification, effect similar to that of the above-described Embodiment 1 can be obtained. Further, according to the first modification, since the residual pressure in the water feeding tank 53 can be released with the water feeding control valve 96w closed, an air feeding action is possible even during releasing the internal pressure of the water feeding tank 53. Therefore, if this configuration is adopted, inconvenience can be eliminated that an air feeding action can not be performed for 2 seconds after an end of a water feeding action as explained in the above description.

Next, with reference to FIG. 13, a second modification of the configuration of the air feeding and water feeding conduit line system in the control unit 3 will be described.

In the second modification, instead of the water feeding control valve 96w and the water feeding tank leak valve 9612 in the above described first modification, one water feeding control valve 96w' is disposed which is configured as a three-port valve having both of these functions.

The water feeding control valve 96w' is configured such that the same can be switched between two states: a first state of communicating the water feeding tank 53 with the pump 99 and a second state of communicating the water feeding tank 53 with the atmosphere.

To perform water feeding, the first state is set so that the water feeding tank 53 and the pump 99 are intercommunicated, and thereby the water feeding tank 53 is pressurized to perform water feeding. To stop water feeding, the second state is set so that the water feeding tank 53 and the atmosphere are intercommunicated, and thereby the internal pressure of the water feeding tank 53 is released.

According to such second modification, effect similar to that of the above-described first modification is obtained as well as saving of space of the control unit 3 is enabled since a number of electromagnetic valves can be decreased.

Of course, the present invention is not limited to the above-described embodiments but various modifications and applications are possible in a scope not departing from a spirit of the invention.

What is claimed is:
1. An endoscope system, comprising:
a two-stage depression button provided in an operation portion of an endoscope;
a first switch disposed at a first stage depressing operation position in the depression button and configured so as to change from off to on by the first stage depressing operation and maintain an on state after the first stage;
a second switch disposed at a second stage depressing operation position in the depression button and configured so as to change from off to on by the second stage depressing operation; and
control means which performs control so as to provide a first function of the endoscope when the first switch is on and provide a second function of the endoscope without providing the first function regardless of a state of the first switch when the second switch is on, the control means performing control so as to provide the first function with a delay of a predetermined time period so long as the first switch does not change from on to off within the predetermined time period when the first switch changes from off to on, the predetermined time period being longer than a time period expected to be required for the depression button to move in a stroke from the first stage to the second stage;

wherein the first function is an air feeding function and the second function is a water feeding function.

2. The endoscope system according to claim 1, wherein the control means performs control so as to provide the first function with a delay of a predetermined time period so long as the first switch does not change from on to off within the predetermined time period when the second switch changes from on to off, the predetermined time period being longer than a time period expected to be required for the depression button to move in a stroke from the second stage to the first stage.

3. The endoscope system according to claim 2, further comprising:
a pump for pressurizing air;
an air feeding control valve which is provided in an air feeding conduit line for performing air feeding from the pump to the endoscope;
a leak valve which is provided in a leak conduit line branching from the air feeding conduit line between the pump and the air feeding control valve;
a water feeding tank; and
a water feeding control valve which is provided in a water feeding tank air feeding conduit line branching from the air feeding conduit line between the pump and the air feeding control valve and being for performing pressurization from the pump to the water feeding tank; wherein
the control means performs control so as to close the leak valve and the air feeding control valve and open the water feeding control valve to perform water feeding from the water feeding tank when the second switch is on, and performs control so as to close the water feeding control valve after a state in which the leak valve is opened with the water feeding control valve being open is continued for a predetermined time period when the second switch changes from on to off.

4. The endoscope system according to claim 2, further comprising:
a pump for pressurizing air;
an air feeding control valve which is provided in an air feeding conduit line for performing air feeding from the pump to the endoscope;
a leak valve which is provided in a leak conduit line branching from the air feeding conduit line between the pump and the air feeding control valve;
a water feeding tank;
a water feeding control valve which is provided in a water feeding tank air feeding conduit line branching from the air feeding conduit line between the pump and the air feeding control valve and being for performing pressurization from the pump to the water feeding tank; and
a water feeding tank leak valve which is provided in a water feeding tank leak conduit line branching from the water feeding tank air feeding conduit line between the water feeding control valve and the water feeding tank; wherein
the control means performs control so as to close the leak valve, the water feeding tank leak valve and the air feeding control valve and open the water feeding control valve to perform water feeding from the water feeding tank when the second switch is on, and performs control so as to close the water feeding control valve and open the water feeding tank leak valve when the second switch changes from on to off.

5. The endoscope system according to claim 2, further comprising:
a pump for pressurizing air;
an air feeding control valve which is provided in an air feeding conduit line for performing air feeding from the pump to the endoscope;
a leak valve which is provided in a leak conduit line branching from the air feeding conduit line between the pump and the air feeding control valve;
a water feeding tank; and
a water feeding control valve which is provided in a water feeding tank air feeding conduit line branching from the air feeding conduit line between the pump and the air feeding control valve and being for performing pressurization from the pump to the water feeding tank, and which is configured so as to be able to be switched between a first state of causing the water feeding tank to communicate with the pump and a second state of causing the water feeding tank to communicate with an atmosphere; wherein
the control means performs control so as to close the leak valve and the air feeding control valve and set the water feeding control valve to the first state to perform water feeding from the water feeding tank when the second switch is on, and performs control so as to set the water feeding control valve to the second state when the second switch changes from on to off.

* * * * *